United States Patent [19]
van der Zel

[11] Patent Number: 5,143,692
[45] Date of Patent: Sep. 1, 1992

[54] METHOD OF MAKING A SUBSTRUCTURE FOR A DENTAL RESTORATION

[75] Inventor: Joseph M. van der Zel, Zwaag, Netherlands

[73] Assignee: Elephant Edelmetaal B.V., Hoorn, Netherlands

[21] Appl. No.: 722,477

[22] Filed: Jul. 2, 1991

[30] Foreign Application Priority Data

Jul. 3, 1990 [NL] Netherlands ............... 9001516

[51] Int. Cl.$^5$ .............................................. G22F 7/00
[52] U.S. Cl. ................................. 419/8; 419/23; 419/36; 419/37; 433/207; 433/208
[58] Field of Search ................... 419/8, 36, 37, 23

[56] References Cited

U.S. PATENT DOCUMENTS

| | | | |
|---|---|---|---|
| 4,011,291 | 3/1977 | Curry | 264/43 |
| 4,742,861 | 5/1988 | Shoher et al. | 164/80 |
| 4,980,124 | 12/1990 | Dimmer | 419/9 |

FOREIGN PATENT DOCUMENTS

714164 11/1941 Fed. Rep. of Germany.
1271157 4/1972 United Kingdom.

*Primary Examiner*—Stephen J. Lechert, Jr.
*Attorney, Agent, or Firm*—Stevens, Davis, Miller & Mosher

[57] ABSTRACT

A method of making a substructure for a dental restoration which comprises a substructure of a dental metal and a fired on coating of a dental ceramics, which method comprises applying a powder-form mixture of a dental metal powder and a thermoplastic polymeric material having a melting point above 50° C., in the shape of the dental restoration to be made, to a porous refractory model, by means of a heated instrument, heating the assembly so obtained to a temperature at which the thermoplastic polymeric material liquefies and is sucked from the coating into the model, followed by raising the temperature of the assembly to a temperature at which the thermoplastic polymeric material disappears, and raising the temperature further to a sintering temperature at which the dental metal powder is sintered into a solid metal mass. The substructure so formed can be provided with a fired on coating of dental ceramics.

39 Claims, 1 Drawing Sheet

METHOD OF MAKING A SUBSTRUCTURE FOR A DENTAL RESTORATION

The invention relates to a method of making a substructure for a dental restoration, such as a crown or a bridge, which dental restoration comprises a substructure of an essentially dental metal and a fired on coating of an essentially dental ceramics, which method comprises applying a material containing a dental metal, in the shape of the dental restoration to the formed, onto a refractory model and heating the assembly obtained to a sufficiently high temperature for sintering the dental metal powder into a solid metal mass.

The method most commonly used heretofore for making dental restorations of metal with a fired on coating of porcelain, comprises casting the alloy according to the so-called "lost wax method", in which a molten alloy is poured into a refractory die which has the shape of the burned-out wax model. The process comprises the following steps:
1. First the dentist takes an impression of the preparation in the mouth using a moulding mass, usually consisting of silicone material.
2. Then, from the impression a positive cast of the model is made in gypsum.
3. Then the dental technician moulds a wax model on the gypsum model.
4. The wax model is provided with supply ducts of wax and embedded in a refractory mass.
5. The die of refractory material is heated to a temperature of from 600 to 1000° C. 6. Then the liquid metal is poured into the cavity formed. During cooling, the cast suffers thermic shrinkage, which must be compensated for by the refractory mass by expansion occurring during heating of the die.
7. The cast workpieces are now finished off with ceramically bound flints or hard metal cutters, optionally followed by coating with porcelain (or more generally with a ceramics material that is suitable for dental applications and will hereinafter be referred to as dental ceramics).

According to various recent publications, process steps 2-6 could be replaced by three steps, viz.:
the impression is cast in a refractory material instead of in gypsum, and the model is burned out at a temperature of from 1000° to 1200° C.; the refractory material may consist of a mixture of quartz sand with a given granule distribution and magnesium oxide and biammonium phosphate as binders; the powder is mixed with colloidal silica to form a slurry; the slurry is poured into the impression and then binds and sets to form a rigid mass within 5 to 10 minutes;
now the metal in powder form is applied to the locations where such is considered necessary for reasons of reinforcement;
the powder applied is sintered at a temperature of from 1000 to 1300° C. to form a solid metal mass.

To prevent oxidation, the last step is usually performed under a vacuum, which can be carried out only in very special ovens designed for the purpose, as described in U.S. Pat. No. 4,702,696. This last is not economically feasible for every laboratory. The high costs make the process unattractive for implementation in the laboratory.

U.S. Pat. No. 3,502,466 describes the making of articles, in particular dental crowns, utilizing metal powders, in particular precious metal powders. The metal powder is first mixed with a binder to form a paste or putty. The binder to be used consists of an adhesive (e.g. ethylcellulose) and a solvent (e.g. propylene glycol). This liquid binder renders moulding laborious and the chances of residual porosity in the final product are substantial.

U.S. Pat. No. 4,661,071 also describes a procedure using powders or mixtures of powders that are utilized according to the above described process for producing dental restorations. However, the method described, too, may require the use of a costly high-vacuum oven, which is not economically feasible for every laboratory. Further, for mixing the powder, use is made of propylene glycol, which yields a paste-like substance. The build up with this liquid is not easy because any excess cannot be removed by dabbing with absorbent paper. It is therefore hard to realize a controlled dense packing of the metal powder and the chance of residual porosity is substantial.

DE 3532331 A1 and DE 3841902 C1 basically describe the same process, except that, as starting material, mixtures of non-oxidizing powders as well as of oxidizable powders are used, which are sintered in a commercial porcelain oven under a graphite bell jar. An important disadvantage of the use of an opaque graphite bell jar is that the restoration during processing is hidden from view. As a result, it cannot be seen if perhaps the restoration makes contact with the graphite bell jar or bottom. Alloys having a palladium content in excess of 35% take up carbon upon contact with graphite at temperatures as used during the heating cycli in oxidizing the restoration and baking the porcelain. A second disadvantage is the burn-out of the outer wall of the graphite bell jar, which is accompanied by crumbling of fine graphite dust, which may contaminate the dental porcelain and the surroundings of the oven. Graphite dust on the restoration may lead to the formation of gas bubbles in the porcelain due to the formation of carbon monoxide gas during baking of the porcelain.

Another disadvantage of the patent cited last is that the metal powders are mixed with a binder consisting substantially of water. The use of water renders the metal powder just as difficult to apply to the model as dental porcelain is, if not more difficult in view of the metal grains rolling over each other. Although the technique of vibrating and dabbing gives a certain degree of densification, it requires special training to densify the metal powder to such an extent that a predictably porosity-free product is obtained.

An important consequence of residual porosity is a brittle product of low ductility. For ductility, the elongation at break of the alloy is considered a standard.

U.S. Pat. No. 4,742,861 describes a method for forming a dental restoration comprising a combination of a high fusing metal component, preferably a combination of gold, platinum and palladium, in a major proportion and a low fusing component, preferably gold. A binder is used to form a kind of putty. For that purpose any organic or synthetic resin can be used, such as ethylene or polyethylene glycol A disadvantage of this procedure is that the liquid binder gives a mixture that is difficult to mould and polish and involves a substantial risk of residual porosity.

In U.S. Pat. No. 4,814,008 use is made of an aggregate of two precious metal powders. A component that makes up 1-15% by volume of the mixture, consists of a powder of platinum or palladium, having a grain size preferably 5-10 times larger than a second finer powder, which preferably consists of gold. During sintering, the mixture is formed into a solid metal. A binder is used which gives the material a paste-like consistency. For that purpose, any organic or synthetic resin can be used, such as ethylene or polyethylene glycol. A disadvantage of this procedure is that the liquid binder yields a mixture that is difficult to mould and to polish and involves a substantial risk of residual porosity.

DE 3811628 A1 describes a process in which metal tooth replacement is realized by means of paste-like metal powders of palladium, gold and silver powder with an average grain size of 0.5-1.5 μm and binders. As a result of its extreme fineness, this powder can only be applied in very thin layers. This renders it impossible to mould occlusions, bridge portions or other solid parts in one step.

This invention solves the disadvantages of the known methods described hereinabove by providing a method of making a substructure for a dental restoration, such as a crown or a bridge, which dental restoration comprises a substructure of an essentially dental metal and a fired on coating of an essentially dental ceramics, which method comprises applying a material containing a dental metal, in the shape of the dental restoration to be formed, onto a refractory model, and heating the assembly obtained to a sufficiently high temperature for sintering the dental metal powder into a solid metal mass, and which method is characterized according to the invention by using, as a material containing a dental metal powder, a mixture of the dental metal powder and a thermoplastic polymeric material having a melting point above 50° C., applying said powder onto a model of a porous refractory material by means of a heated instrument, for instance a waxing knife, and moulding it into the desired shape, heating the assembly so obtained to a temperature at which the thermoplastic polymeric material liquefies and is sucked from the coating into the model, followed by raising the temperature of the assembly to a temperature where the thermoplastic polymeric material disappears, and raising the temperature further to a sintering temperature.

According to the invention, it is preferable to use, as the material containing a dental metal powder, a mixture consisting as to 75-99% by weight of the dental metal and as to 1-25% by weight of a thermoplastic polymeric material having a melting point above 50° C. It is more preferable to use, as the material containing a dental metal powder, a mixture consisting as to 85-97% by weight of the dental metal and as to 3-15% by weight of a thermoplastic polymeric material with a melting point above 50° C.

Although any thermoplastics with a melting point above 50° C., preferably above 60° C., can be used as the thermoplastic polymeric material, it is particularly preferable, and in accordance with the invention, to use as the thermoplastic polymeric material, a wax with a melting point above 60° C., for instance a high-melting amide wax. Examples of other usable thermoplastic polymeric materials are agar-agar, paraffins, polyethylene, polypropene, polybutene, polystyrene, ethylenevinyl acetate copolymers, isotactic polypropene/wax-/stearate copolymers, isotactic polypropene/atactic polypropene/stearate copolymers, methylcellulose, polybutylmethacrylate, cellulose acetate, hydroxyethylcellulose, acryl resins, polyvinyl alcohol, polyvinyl pyrrolidon, and the like.

As to the powder of dental metal, it is preferable, according to the invention, to use a dental metal powder having a particle size of at most 100 μm, preferably at most 75 μm. More particularly, preferably a dental metal powder is used with a median particle size of 5-50 μm, preferably 10-35 μm.

Although any conventional dental metal powder can be used, it is preferable, according to the invention, that a dental metal powder is used as defined in applicant's Netherlands patent application 90.00189, the contents of which is considered incorporated herein by reference. Thus, according to the invention, it is preferable to use a dental metal powder comprising a core consisting essentially of a dental metal, which core is coated with one or more layers consisting essentially of metal, which layers protect the dental metal of the core against oxidation during sintering and/or lower the temperature at which sintering of the powder occurs. More particularly, it is preferable that the coating of the dental metal core, consisting of one or more metal layers, comprises at least one layer consisting of either (a) a metal having a lower melting point than the dental metal of the core, or (b) a metal capable of reacting with the dental metal of the core or with a metal of an adjacent coating layer to form a material having a lower melting point than the dental metal of the core.

It is recommendable that the coating of the dental metal core, consisting of one or more layers, comprises at least one layer of a precious metal or of a non-oxidizing precious metal alloy. Preferably, the coating of the dental metal core, consisting of one or more metal layers comprises at least one layer of gold, palladium, platinum, iridium, rhodium, or ruthenium. More preferably, the coating of the dental metal core, consisting of one or more layers, comprises at least one layer, provided on the inside, of copper, nickel, indium, tin, gallium, or zinc, as well as at least one layer provided on the outside, of gold, palladium, platinum, iridium, rhodium, or ruthenium. Thus, it is quite concretely possible that the coating of the dental metal core, consisting of one or more metal layers, comprises at least one layer of palladium, provided on the inside, as well as at least one layer of gold, provided on the outside.

The dental metal of the core preferably consists of a platinum-gold dental alloy, a palladium-gold dental alloy, a high-palladium dental alloy, a silver-palladium dental alloy, or of titanium metal. Thus, a suitable option is for the core to consist of a platinum-gold dental alloy, a palladium-gold dental alloy, a high-palladium dental alloy, or a silver-palladium dental alloy, which core is successively coated with a layer of palladium and a layer of gold. Another real option, however, is that the core consists of titanium metal and the core is successively coated with a layer of copper or nickel, a layer of palladium and optionally a layer of gold.

It is preferable that the core coating, consisting of one or more layers, constitutes 1-50% by volume, preferably 5-25% by volume, of the powder, and that the core coating, consisting of one or more layers, has a thickness of 1-75 μm, preferably 5-65 μm.

Further, according to the invention, it is preferable to use a dental powder which is a mixture of a powder-form dental alloy having an average particle size of 5-50 μm and 1-15% by weight of chemically precipitated, spherical gold powder of a grain size of 0.5-15 μm. Utilizing such a mixture may prevent crack formation in the sintered product. Mixing with a thermoplastic polymer prevents the separation of the relatively fine, chemically precipitated gold powder and the coarser alloy powder, formed, for instance, by atomization of the melt with the aid of a gas jet.

A very particular preferred embodiment of the invention is characterized by applying the dental metal powder on the model after first applying a thin bonding layer on the model, which bonding layer comprises a mixture of a dental metal and a glasslike or ceramics material.

In that embodiment it is preferable, according to the invention, to use, as a bonding layer, a mixture consisting as to 10-90% by weight, preferably 20-80% by weight, of a dental metal powder and as to 10-90% by weight, preferably 20-80% by weight, of a powder of glasslike or ceramics material.

The glasslike or ceramics material will preferably be a high-melting porcelain. All types of porcelain known in the field of dental technique are suitable for this purpose. The powder cf glasslike or ceramics material and the dental metal powder preferably have a particle size of at most 10 $\mu$m, preferably at most 5 $\mu$m.

The mixture is preferably applied to the model in a liquid state, obtained by mixing a mixture of the dental metal powder and the powder of glasslike or ceramics material, with a liquid carrier, such as polyethylene glycol.

The bonding layer will preferably have a thickness of at most 50 $\mu$m, preferably at most 30 $\mu$m.

After the bonding layer has been applied, the temperature of the model with the bonding layer applied thereto, is raised to a temperature at which the liquid carrier disappears, and subsequently raised further to a sintering temperature, for instance a temperature of 900°-1300° C.

After the powder mixture of dental metal and thermoplastic polymeric material has been applied on the sintered assembly of the model and the thin bonding layer applied thereto, the temperature is first raised to approximately 50°-100° C. so as to suck the thermoplastic polymeric material into the pores of the model through capillary activity, then the temperature is raised to approximately 150°-500° C. to cause the thermoplastic polymeric material to disappear by burning, and thereafter the temperature is further raised to a sintering temperature of, e.g., 900°-1300° C.

In a particular preferred embodiment of the invention, a sintering operation is carried out in an oven in which the article to be sintered is arranged on a graphite bottom, while it is separated from the surrounding atmosphere by a quartz glass bell jar. Oxidation of the metal powder can thereby be avoided, and still the restoration remains visible as much as possible during processing. At the same time, the surroundings of the oven are less contaminated by graphite dust.

It will be clear the invention further extends to a method of making a dental restoration, such as a crown or a bridge, in which a substructure essentially consisting of a dental metal, made by the use of the method according to the invention described hereinabove, is provided with a fired on coating of dental ceramics in a manner known per se.

BRIEF DESCRIPTION OF THE DRAWINGS

The apparatus aspect of the present invention will be more fully described in accordance with the drawings in which.

Figure 1:
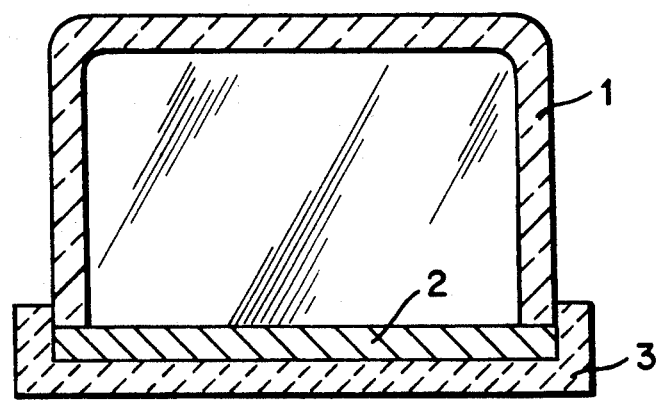
FIG. 1 shows a bell jar in which the restoration is treated.

In summary, the invention described herein concerns the use for the sintering process of a metal powder consisting of a conventional dental alloy with an adjusted grain distribution, which is mixed with a thermoplastic binder, such as high-melting wax. As a base, a special fine-grained and porous refractory mass is used. During heating of the restoration, the wax liquefies at a temperature of, e.g., 80°-100° C. and penetrates into the porous base as a result of the capillary activity of the fine porous refractory mass. As a result of the disappearance of the wax from the restoration into the refractory base, the fine metal powder is strongly densified and a virtually perfect dense grain packing is obtained, which in other methods, such as serrating or dabbing, can only be achieved with difficulty. After further burn-out of the wax, the restoration is placed under a bell jar consisting of low-expansion quartz glass (1) with a graphite plate (2) as a bottom (see FIG. 1). the graphite bottom is inlaid in a bowl of refractory material (3) to prevent graphite contamination in the over. Because the graphite has practically no contact with the ambient atmosphere, this bottom plate will burn out only slowly. The glass bell jar must be fitted tightly against the graphite plate to prevent oxygen in the air from leaking in. Oxidation of the alloy leads to a brittle product of low sintering density.

For the metal powder, preferably powders of dental alloys are used, with the outer surface of the powder grains being provided with one or more dense metal layers of an alloy or a metal having a low oxidation tendency and a lower melting point than the alloy of the metal of the powder itself, as described in applicant's older Netherlands patent application 90.00189, the contents whereof is considered incorporated herein by reference.

In the process, all dental alloys can be utilized which have been developed for the porcelain-metal technique over the past decades. These alloys have proved themselves in clinical conditions and are well documented as to composition and biological properties. The layers applied by means of galvanizing or cathode sputtering techniques, preferably consist of gold or palladium, or of a mixture of the two. Other non-oxidizing elements can be used as well, as long as their melting point is below that of the alloy to be covered.

By virtue of the dense layer or layers applied, it is no longer necessary to sinter under a high vacuum, and sintering can be done using an ordinary porcelain oven, which yields an important economic advantage over the use of special apparatus. Further, by virtue of the invention disclosed in applicant's Netherlands patent application 90.00189, it is possible to use alloys or metals that are hardly castable, if at all. The powder must have a packing density of preferably approximately 75%, so as to permit sufficient capillary flow of a thermoplastic binder through the powder during the further course of the process. Too low a grain packing leads to a less dense product, while a higher grain packing or too fine a grain packing causes too low a mobility of the thermoplastic binder.

Figure 2:
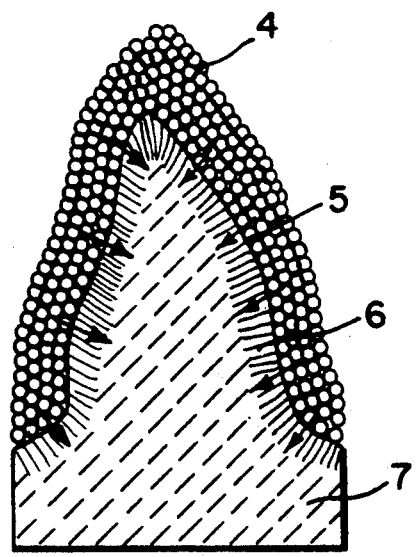
FIG. 2 shows the wax migration from the metal powder into an impregnation zone.

The metal powder is mixed with 1-25% by weight of a high fusing wax, for instance with 4-5% of wax. For that purpose, the powder metal is heated in a beaker together with the weighed out amount of wax, until the wax melts, and the mixture is stirred until the wax is distributed homogeneously throughout the metal. This mixture allows application on the porous, fine-grained refractory model, as is now done by a dental technician in moulding a wax model on a gypsum model. A preferably electrically heated waxing knife with a temperature of, for instance, approximately 150° C., is used for applying and smoothing the metal/wax mixture. After moulding, the metal/wax model can be polished until the outer surface is smooth. Modification is possible at all times, should such prove necessary upon subsequent checking of the model. In that event, the model is, for instance, arranged under an oven chamber opened at the lower end and preheated to 450° C. As the temperature of the model rises, the viscosity of the wax becomes sufficiently low, thus permitting capillary flow. Owing to the high porosity and the fine grain size of the subjacent refractory model mass, the wax flows from the metal powder into the refractory mass by capillary attraction. Thus, a capillary attraction between the metal grains is achieved by the migration of the binder in one direction (perpendicular to the refractory surface). FIG. 2 shows how the wax migrates from the metal powder (4) into the refractory model (7) from the wax/metal zone (5) into an impregnation zone (6).

EXAMPLE

A refractory model was fabricated according to standard laboratory methods. First of all, a duplicate mould of addition hardening silicone mass was made. The duplicate mould was then treated with a surface expanding agent and the excess was blown off. The duplicate stump was then cast in a model mass mixed with colloidal silica, consisting of quartz, bonded with 15% magnesium oxide and 15% biammonium phosphate. The grain size distribution of the refractory mass was determined by the ratio of the added sieve fractions. Thus, a desirable high porosity of the refractory mass could be achieved.

First of all, 20 g refractory model mass was mixed with 4 ml mixing fluid (20% colloidal silica) under a vacuum for 30 sec. The mixed embedding mass was poured into the duplicate mould with vibration. After 30 min, the model was removed from the mould by means of compressed air. At all locations on the model where metal was to be subsequently applied, a thin bonding layer of a bonding agent was applied, consisting of a mixture of high fusing porcelain and a fine metal powder. The high fusing porcelain had the following formulation: 65% $SiO_2$, 16% $Al_2O_3$, 12% $K_2O$, 6% $Na_2O$, and 1% $CaO$. After fusion of the components in a platinum crucible at 1600° C. for 4 hours, the porcelain was cast in water. Then it was ground in an attritor grinder to a fineness of less than 1 $\mu$m. The metal powder could consist of a fine-grained alloy powder of a grain size smaller than 10 $\mu$m or of a precious powder, prepared by chemical precipitation from a solution, of a grain size of preferably less than 5 $\mu$m. Eminently suitable was a 60:40 mixture (on weight basis) of chemically precipitated gold and palladium. The porcelain was mixed with such a metal powder in a volume ratio of 1:1. The mixture was mixed with polyethylene glycol to form a creamy substance and applied to the model in a thin layer, predried for 10 min under an opened oven chamber preheated to 700° C., followed by baking at 1100° C. for 2 min.

An alloy powder was selected of a grain size of at most 45 $\mu$m and a median grain size of 27 $\mu$m. The composition of the alloy was 53.5% palladium, 37.5% silver, 8.5% tin and 0.5% indium. This alloy was mixed with a chemically precipitated, spherical gold powder of an average grain size of 10 $\mu$m. The packing density was 75%.

The powder was mixed with 3.5% ACRAWAX B (a commercial product of Glyco Chemicals, Inc., USA, which is a reaction product of a stearic acid and monoethanolamine having a fusing point between 83 and 86° C. and a flash point in air of 235° C.; this thermoplastic polymer forms a gel with kerosene). The powder was stirred with a warm waxing knife until the wax was homogeneously distributed through the metal powder. Then, the powder was applied to the refractory model with an electric waxing instrument (set at 150° C). The crown was moulded completely and its shape checked in an articulator. The finished moulded crown remained on the stump throughout the sintering process. To evaporate the wax, the restoration was arranged on a graphite bottom under an opened oven chamber preheated to 450° C. (then on the table a temperature of 75° C. prevailed) until a change in the colour of the powder occurred and the moulding "smoothened" at the surface. At this point, the wax migrated into the refractory model. The temperature of the oven was then raised to 1000° C. (corresponding to a temperature of 360° C. on the table). At an oven temperature of 700° C., small clouds of smoke became visible. As the temperature rose to 1000° C., smoke production increased until it stopped practically completely after approximately 5 min. Then there was a 15 to 25-minute waiting interval and a quartz glass bell jar was arranged over the graphite bottom plate. The powder was sintered under a vacuum at 1130° C. for 15 min. After sintering had been completed, the oven was opened and the restoration was cooled under the quartz glass bell jar.

In this manner, five test rods of 2×6×14 mm were sintered and subjected to a three-point bending test (support distance 10 mm). A clear plastic deformation was observed before the rods broke at a bending strength of 700 MPa (Standard Deviation=120 MPa).

I claim:

1. A method of making a substructure for a dental restoration, which dental restoration has a substructure of an essentially dental metal and, fired thereon, a coating of an essentially dental ceramics, comprising applying a mixture of a dental metal powder and a thermoplastic polymeric material having a melting point above 50° C. onto a model of a porous refractory material by means of a heated instrument and molding said mixture into a desired shape to form an assembly, heating the assembly so obtained to a temperature at which the thermoplastic polymeric material liquefies and is absorbed from the coating into the model, followed by raising the temperature of the assembly to a temperature at which the thermoplastic polymeric material is expelled from the assembly, and raising the temperature further to a sufficiently high temperature for sintering the dental metal powder into a solid metal mass.

2. The method as claimed in claim 1, wherein said mixture comprises 75-99% by weight of said dental metal powder and 1-25% by weight of said thermoplastic polymeric material having a melting point above 50° c.

3. The method as claimed in claim 1, wherein said mixture comprises 85-97% by weight of said dental metal powder and 3-15% by weight of said thermoplastic polymeric material having a melting point above 50° c.

4. The method as claimed in claim 1, wherein a wax having a melting point above 60° C. is used as the thermoplastic polymeric material.

5. The method as claimed in claim 1, wherein said dental metal powder has a particle size of at most 100 μm.

6. The method as claimed in claim 1, wherein said dental metal powder has a particle size of at most 75 μm.

7. The method as claimed in claim 1, wherein said dental metal powder has a median particle size of 5–50 μm.

8. The method as claimed in claim 1, wherein said dental metal powder has a median particle size of 10–35 μm.

9. The method as claimed in claim 1, wherein said dental metal powder comprises a core consisting essentially of a dental metal, which core is coated with one or more layers consisting essentially of metal, which layers protect the dental metal of the core against oxidation during sintering, lower the temperature at which sintering of the powder occurs, or both.

10. The method as claimed in claim 9, wherein said coating of the dental metal core, consisting of one or more metal layers, comprises at least one layer consisting of either (a) a metal having a lower melting point than the dental metal of the core, or (b) a metal capable of reacting with the dental metal of the core or with a metal of an adjacent coating layer to form a material having a lower melting point than the dental metal of the core.

11. The method as claimed in claim 9, wherein said coating of the dental metal core, consisting of one or more metal layers, comprises at least one layer of a precious metal or a non-oxidizing precious metal alloy.

12. The method as claimed in claim 9, wherein said coating of the dental metal core, consisting of one or more metal layers, comprises at least one layer of gold, palladium, platinum, iridium, rhodium, or ruthenium.

13. The method as claimed in claim 9, wherein said coating of the dental metal core, consisting of one or more metal layers, comprises at least one inner layer of copper, nickel, indium, tin, gallium, or zinc, as well as at least one outer layer of gold, palladium, platinum, iridium, rhodium, or ruthenium.

14. The method as claimed in claim 9, wherein said coating of the dental metal core, consisting of one or more metal layers, comprises at least one inner layer of palladium, as well as at least one outer layer of gold.

15. The method as claimed in claim 9, wherein said dental metal of the core consists of a platinum-gold dental alloy, a palladium-gold dental alloy, a high-palladium dental alloy, a silver-palladium dental alloy or of a titanium metal.

16. The method as claimed in claim 9, wherein said core consists of a platinum-gold dental alloy, a palladium-gold dental alloy, a high palladium dental alloy, or a silver-palladium dental alloy, which core is successively coated with a layer of palladium and a layer of gold.

17. The method as claimed in claim 9, wherein said core consists of titanium metal and the core is successively coated with a layer of copper or nickel and a layer of palladium.

18. The method as claimed in claim 9, wherein sad core consists of titanium metal and the core is successively coated with a layer of copper or nickel, a layer of palladium and a layer of gold.

19. The method as claimed in claim 9, wherein said core consisting of one or more layers constitutes 1–50% by volume of said powder.

20. The method as claimed in claim 9, wherein said core consisting of one or more layers constitutes 5–25% by volume of the powder.

21. The method as claimed in claim 9, wherein said coating of the core, consisting of one or more layers, has a thickness of 1–75 μm.

22. The method as claimed in claim 9, wherein said coating of the core, consisting of one or more layers, has a thickness of 5–65 μm.

23. The method as claimed in claim 1, wherein said dental metal powder is a mixture of a dental alloy powder having an average particle size of 5–50 μm and 1–15% by weight of a chemical precipitated, spherical gold powder having a grain size of 0.5–15 μm.

24. The method as claimed in claim 1, including applying a thin bonding layer on the model before said dental metal powder is applied, which bonding layer comprises a mixture of a dental metal and a glasslike or ceramic material.

25. The method as claimed in claim 24, wherein said bonding layer is a mixture comprising 10–90% by weight of a dental metal powder and 10–90% by weight of a powder of glasslike or ceramic material.

26. The method as claimed in claim 24, wherein said bonding layer is a mixture comprising 20–80% by wight of a dental metal powder and 20–80% by weight of a powder of glasslike or ceramic material.

27. The method as claimed in claim 24, wherein said glasslike or ceramic material consists of a high-melting porcelain.

28. The method as claimed in claim 24, wherein said powder of glasslike or ceramic material and the dental metal powder have a particle size of at most 10 μm.

29. The method as claimed in claim 24, wherein said powder of glasslike or ceramic material and the dental metal powder have a particle size of at most 5 μm.

30. The method as claimed in claim 24, wherein sad mixture is applied onto the model in a liquid state, obtained by mixing a mixture of the dental metal powder and the powder of glasslike or ceramic material with a liquid carrier.

31. The method as claimed in claim 24, wherein said mixture is applied onto the model in a liquid state, obtained by mixing a mixture of the dental metal powder and the powder of glasslike or ceramic material with the liquid carrier consisting of polyethylene glycol.

32. The method as claimed in claim 24, wherein said bonding layer has a thickness of at most 50 μm.

33. The method as claimed in claim 24, wherein said bonding layer has a thickness of at most 30 μm.

34. The method as claimed in claim 30, wherein the temperature of the model with the bonding layer applied thereto is raised to a temperature at which the liquid carrier is expelled and then is further raised to a sintering temperature.

35. The method as claimed in claim 30, wherein the temperature of the model with the bonding layer applied thereto is raised to a temperature at which the liquid carrier is expelled and then is further raised to a sintering temperature in the range of 90°–1300° C.

36. The method as claimed in claim 24, wherein, after the powder mixture of dental metal and thermoplastic polymeric material has been applied to the assembly of the model and the thin bonding layer applied thereto, the temperature is first raised to about 50–100° C. to absorb the thermoplastic polymeric material into the pores of the model through capillary activity, the temperature is then raised to about 150°-500° C. to expel the thermoplastic polymeric material, and thereafter the temperature is further raised to a sintering temperature.

37. The method as claimed in claim 24, wherein, after the powder mixture of dental metal and thermoplastic polymeric material has been applied to the assembly of the model and the thin bonding layer applied thereto, the temperature is first raised to about 50°-100° C. to absorb the thermoplastic polymeric material into the pores of the model through capillary activity, the temperature is then raised to about 150°-500° C. to expel the thermoplastic polymeric material, and thereafter the temperature is further raised to a sintering temperature in the range of 900°-1300° C.

38. The method as claimed in claim 1, wherein said sintering operation is carried out in an oven in which the article to be sintered is arranged on a graphite bottom, while being separated from the surrounding atmosphere by a quartz glass bell jar.

39. The method of making a dental restoration, which dental restoration comprises a substructure of an essentially dental metal and, fired thereon, a coating of an essentially dental ceramics, wherein a coating of dental ceramics is fired on a substructure made by the method as claimed in claim 1.

* * * * *